United States Patent [19]

Malone et al.

[11] Patent Number: 4,921,858

[45] Date of Patent: May 1, 1990

[54] 7-DEAZAGUANINES AS IMMUNOMODULATORS

[75] Inventors: Thomas C. Malone, Canton; Jagadish C. Sircar, Ann Arbor, both of Mich.

[73] Assignee: Warner-Lambert Company, Morris Plains, N.J.

[21] Appl. No.: 354,312

[22] PCT Filed: Oct. 19, 1987

[86] PCT No.: PCT/US87/02727

§ 371 Date: Mar. 13, 1989

§ 102(e) Date: Mar. 13, 1989

[87] PCT Pub. No.: WO88/03142

PCT Pub. Date: May 5, 1988

Related U.S. Application Data

[63] Continuation of Ser. No. 86,231, Aug. 20, 1987, abandoned, which is a continuation-in-part of Ser. No. 923,521, Oct. 24, 1986, abandoned.

[51] Int. Cl.$^5$ .................. A61K 31/505; C07D 487/04
[52] U.S. Cl. ............................. 514/258; 544/280; 544/316; 544/330; 544/331
[58] Field of Search .................... 514/258; 544/280

[56] References Cited

U.S. PATENT DOCUMENTS

| | | | |
|---|---|---|---|
| 4,061,753 | 12/1977 | Bodor et al. | 544/271 |
| 4,140,851 | 2/1979 | Townsend | 536/24 |
| 4,229,453 | 10/1980 | Roth et al. | 544/280 |
| 4,435,569 | 3/1984 | Nishimura et al. | 544/280 |
| 4,435,570 | 3/1984 | Nishimura et al. | 544/280 |
| 4,571,423 | 2/1986 | Nomura et al. | 544/280 |
| 4,650,868 | 3/1987 | Nishimura et al. | 544/280 |
| 4,772,606 | 9/1988 | Sircar et al. | 544/261 |

FOREIGN PATENT DOCUMENTS 156559 10/1985 European Pat. Off. .
2574407 6/1986 France .

OTHER PUBLICATIONS

Noell et al., *J. Het. Chem.* pp. 34–41 (1964).
Derwent Abstract for NE 6407785 (1/13/65).
Derwent Abstract for GB 981458 (1/27/65).
Derwent Abstract for EP57548 (8/11/82).
Derwent Abstract for DE 3036390 (5/13/82).
Derwent Abstract for EP 79447 (5/25/83).
Derwent Abstract for DE 3145287 (5/19/83).
Derwent Abstract for EP 89055 (9/21/83).
Derwent Abstract for JP 59/036615 (2/28/84).
Derwent Abstract for EP 119591 (9/26/84).
Derwent Abstract for JP 60/204788 (10/16/85).
Derwent Abstract for EP 160910 (11/13/85).
*The Merck Manual* (14th. Ed.) pp. 328–331 (1982).
*Scientific American Medicine,* pp. 1 and 5 (1987).
Kazmers et al, *Science,* 214, pp. 1137–1139 (1981).
*The Merck Index* (11th Ed.), p. 431, No. 2759 (1989).
White et al., *Transplantation Proceedings,* vol. XI p. 855 (1979).
Borel et al., *Immunology,* p. 1017 (1977).
Assan et al., *The Lancet,* p. 57 (1985).
Austen et al., *New England Journal of Medicine* p. 1436 (1984).
Ellis et al., *JAMA,* 256, p. 3110 (1986).
Legravereno et al., *Tet. Lett.* 26 pp. 2001–2002 (1985).

*Primary Examiner*—Mukund J. Shah
*Assistant Examiner*—E. Bernhardt
*Attorney, Agent, or Firm*—Joan Thierstein

[57] ABSTRACT

The present invention is various 7-deazaguanines having activity as immunomodulators. Also included are pharmaceutical compositions and methods of use thereof.

8 Claims, No Drawings

7-DEAZAGUANINES AS IMMUNOMODULATORS

This is a continuation of PCT/US 87/0727 filed Oct. 19, 1987 which is a continuation of 07/086,231 filed Aug. 20, 1987, now abandoned, which is a continuation-in-part of U.S. application Ser. No. 923,521 filed Oct. 24, 1986, now abandoned.

BACKGROUND OF THE INVENTION

The pyrrolo[2,3-d]pyrimidin-4-ones of the following formula 2, 3 and 4

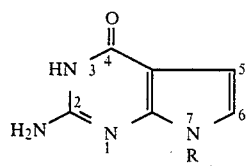

2, R is n-C$_3$H$_7$
3, R is CH$_2$C$_6$H$_5$
4, R is cyclopentyl are known, R. K. Robins, et al, synthesized the compounds of formula 2 and 3 as reported in *J. Het. Chem.*, 1964, 34, but gave no biological activity for either compound. M. Legraverend, et al, reported the synthesis of the compounds of formula 3 and 4 in *Tetrahedron Letters*, 1985, 2001, but again gave no biological activity for either compound.

Of lesser interest the following references provide a background in which a 7-(substituted phenyl)pyrrolo[2,3-d]pyrimidin-4-one having a methyl at each of the five (5) and six (6) positions for treating CNS illnesses or inflammations is disclosed generically in U.S. Pat. No. 4,229,453. Similarly, 4-mercapto-7-(phenyl substituted or unsubstituted)pyrrollo [2,3-d]pyrimidine derivatives requiring an alkyl or phenyl at the five (5) and six (6) positions are disclosed in German 3145287 (Derwent Abstract No. 49344 K/21). Other pyrrolo[2,3-d]pyrimidin-4-one or thione, distinguished by having various substituents at the five (5) position, are found in U.S. Pat. Nos. 4,435,570 and 4,140,851; European publications 160,910 (Derwent Abstract No. 85-284574/46); 89,055 (corresponding to U.S. Pat. No. 4,571,423); 119,591 (Derwent Abstract No. 84-238735/39); 79,447 (corresponding to U.S. Pat. No. 4,435,569); German 3,306-390 (Derwent Abstract No. 39438 E/20); German 3145287 (Derwent Abstract No. 49344 K/21); British Pat. No. 981,458 (Derwent Abstract No. 15,454); Japanese J6 0204,788 (Derwent Abstract No. 85/298810/48); and Japanese J5 9036615 (Derwent Abstract No. 84-086061/84).

Finally, hydroxy and mercapto analogs of the antibiotic sparsomycin A are pyrrolo[2,3-d]pyrimidin-4-one or thione having a sugar moiety in the seven (7) position are disclosed by Upjohn in Netherlands 6,407,785 (Derwent Abstract No. 15,466) and similarly by Warner Lambert in European publication 57,548 (Derwent Abstract No. 68572 E/33).

Copending Applications Ser. No. PD-3557 and Ser. No. 767,202 filed Aug. 22, 1985, now U.S. Pat. No. 4,772,606, which is a continuation-in-part of U.S. Ser. No. 660,152 filed Oct. 12, 1984, now abandoned, disclose similar activity as now found in the present invention for different ring systems.

SUMMARY OF THE INVENTION

The present invention relates to a compound of the formula (I)

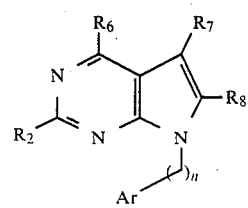

wherein R$_6$ is OH or SH, R$_2$ is hydrogen or NH$_2$, R$_7$ and R$_8$ are independently hydrogen or NH$_2$ with the proviso that both cannot be NH$_2$ at once, n is an integer of from one through four, Ar is (i) phenyl unsubstituted or substituted by halogen, trifluoromethyl, alkyl of one to four carbon atoms, hydroxy, or alkoxy of from one to four carbon atoms, (ii) 2- or 3-thienyl, or (iii) 2- or 3-furanyl with the proviso that when R$_6$ is OH, and R$_2$ is H$_2$N, and R$_7$ and R$_8$ are both hydrogen then Ar cannot be unsubstituted phenyl; or a pharmaceutically acceptable base or acid addition salt thereof.

The present invention also includes methods of manufacturing and novel intermediates therein, and a pharmaceutical composition for treating autoimmune diseases such as arthritis, systemic lupus erythematosus, inflammatory bowel diseases, juvenile diabetes, myasthenia gravis, multiple sclerosis, gout and gouty arthritis, as well as psoriasis, viral infections and cancer, or rejection of transplantation, comprising an antipsoriatic, immunomodulator or antirejection effective amount such as an advantageously cytotoxic to T-cell amount, of a compound of the formula (I)

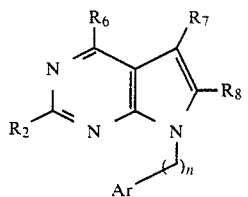

or a pharmaceutically acceptable base or acid addition salt thereof wherein R$_6$ is OH or SH, R$_2$ is hydrogen or NH$_2$, R$_7$ and R$_8$ are independently hydrogen and NH$_2$ with the proviso that both cannot be NH$_2$ at once, n is an integer of from one to four, Ar is (i) phenyl unsubstituted or substituted by halogen, trifluoromethyl, alkyl of one to four carbon atoms, hydroxy, alkoxy of from one to four carbon atoms, (ii) 2- or 3-thienyl, or (iii) 2- or 3-furanyl with a pharmaceutically acceptable carrier. Thus, the invention is also a method of treating psoriasis, an autoimmune disease, such as is listed above, or rejection of transplantation comprising administering to a host, such as a mammal including a human, suffering from psoriasis, the autoimmune disease or rejection of transplantation comprising administering an effective amount; i.e. an amount advantageously affecting T-cells by toxicity thereto, of a pharmaceutical composition of the formula I as defined above in unit dosage form. It is understood, an ordinarily skilled physician would begin treatment with a less than effective amount and increase the dose until the desired effect is obtained exercising care to administer an amount less than the amount toxic to the host of the disease.

The novel intermediates of the present invention are compounds of formula (X)

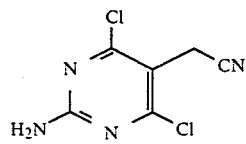

X

The method of manufacture of the present invention is a novel process for the preparation of a compound of the formula I as defined above; which comprises treating a compound of the formula (X)

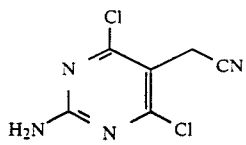

X with a compound of the formula (V)

V wherein Ar and n are as defined above and then treating with an acid to obtain the compound of formula I wherein $R_6$ is oxygen and $R_8$ is $NH_2$ and alternatively, if desired, further deaminating by known methods or treating also by known methods, to obtain a compound of formula I wherein $R_6$ is sulfur and then, if desired, deaminating.

The compound of formula X is prepared by treating a compound of the formula (IX)

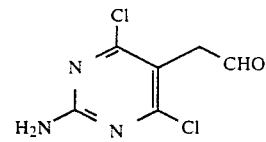

IX with a cyanation agent, such as O,N-bistrifluoroacetyl-hydroxylamine, in the presence of a base, such as pyridine to obtain the compound of formula X.

The above preparations use standard synthetic techniques or techniques as shown or similar to those as shown in the examples hereinafter. The starting materials for the preparation are readily available, known or can be prepared by known methods.

The methods of manufacture for the compounds of the present invention are summarized in the following Schemes I and II.

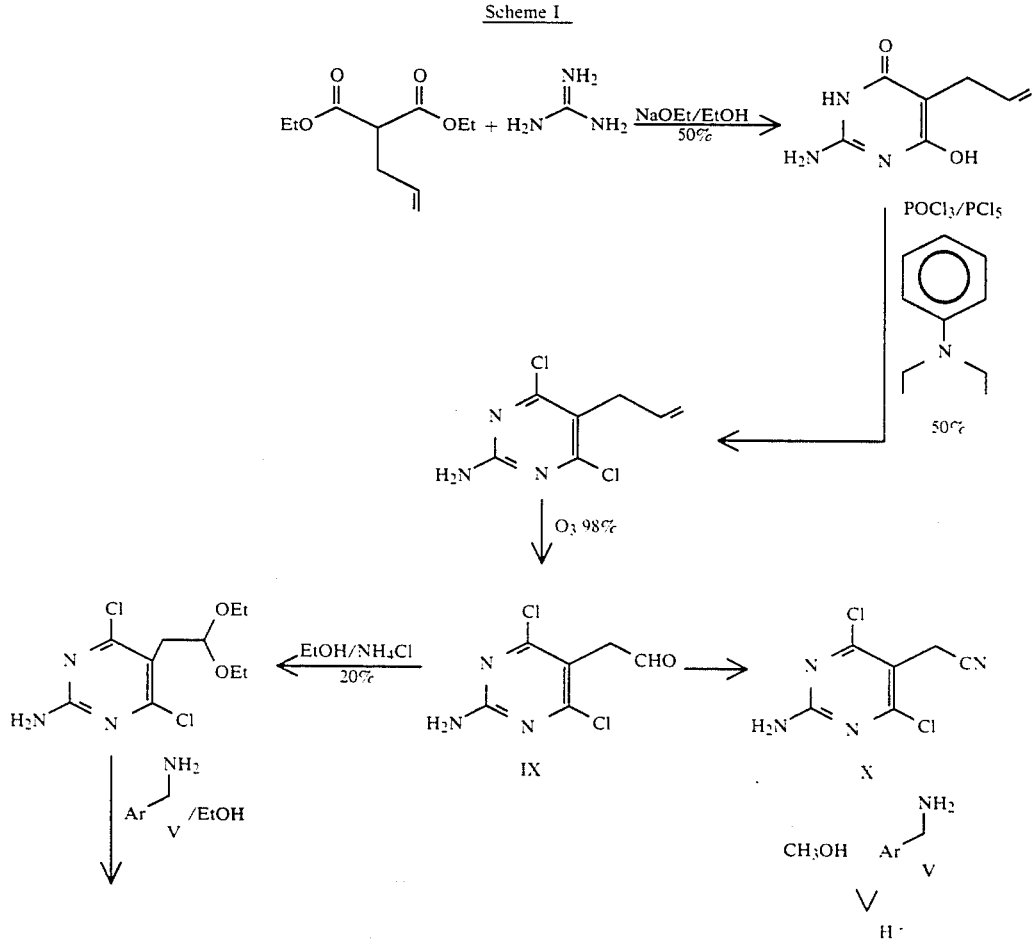

Scheme I

-continued
Scheme I

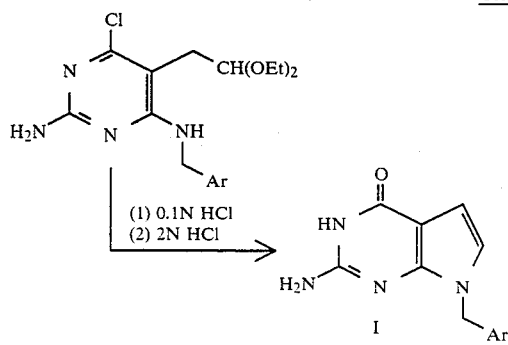

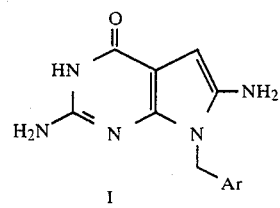

wherein $R_2$ is $NH_2$, $R_6$ is O,
$R_7$ is hydrogen and $R_8$ is $NH_2$ wherein $R_2$ is $NH_2$, $R_6$ is O,
and $R_7$ and $R_8$ are both hydrogen Scheme II

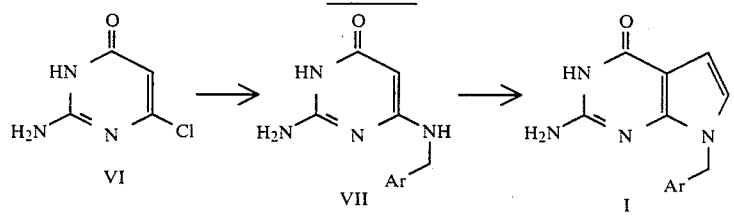

wherein $R_2$ is $NH_2$ and
$R_8$ and $R_7$ both are
hydrogen and $R_6$ is O

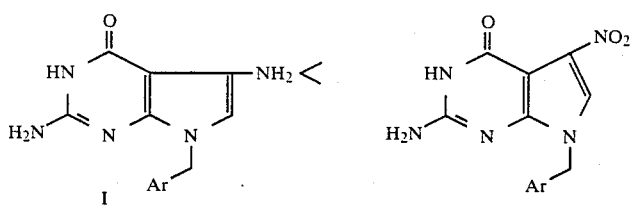

wherein $R_2$ is $NH_2$, $R_6$
is O, $R_7$ is $NH_2$ and
$R_8$ is hydrogen

Under certain circumstances it may be necessary to protect either the N or O of intermediates in the above noted process with suitable protecting groups which are known. Introduction and removal of such suitable oxygen and nitrogen protecting groups are well-known in the art of organic chemistry; see for example, (1) "Protective Groups in Organic Chemistry," J. F. W. McOmie, ed., (New York, 1973), pp 43ff, 95ff; (2) J. F. W. McOmie, *Advances in Organic Chemistry*, Vol. 3, 191–281 (1963); (3) R. A. Borssonas, *Advances in Organic Chemistry*, Vol. 3, 159–190 (1963); and (4) J. F. W. McOmie, *Chem. & Ind.*, 603 (1979).

Examples of suitable oxygen protecting groups are benzyl, t-butyldimethylsilyl, methyl, isopropyl, ethyl, tertiary butyl, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

The salts of compounds of formula I described above are prepared by reacting the appropriate base with stoichometric equivalent of the acid compounds of formula I to obtain pharmacologically acceptable salts thereof.

The compounds of this invention may also exist in hydrated or solvated forms.

DETAILED DESCRIPTION

The compounds of formula I of the present invention exist in tautomeric forms as purines or guanines as illustrated below. Both forms are included as part of the invention and are indiscriminately described in the specification.

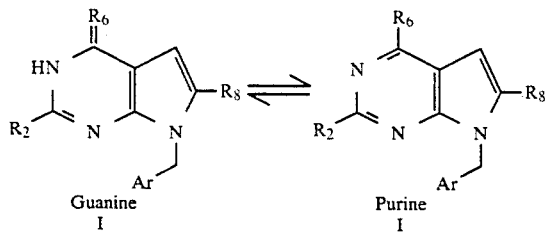

Guanine
I

Purine
I

The term "alkyl of one to four carbon atoms" means a straight or branched hydrocarbon chain up to four carbon atoms such as, for example, methyl, ethyl, propyl, isopropyl, butyl, isobutyl, secondary butyl or tertiary butyl. Alkoxy of one to four carbon atoms includes methoxy, ethoxy, propoxy, butoxy and isomers thereof. Halogen is fluorine, chlorine, bromine, or iodine.

The compounds of formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hyrochloric acid and sulfuric acid, and organic acids such as methanesulfonic acid, benzenesulfonic acid, p-toluenesulfonate, and the like, respectively, or those derived from bases such as suitable organic and inorganic bases. Examples of suitable inorganic bases for the formation of salts of compounds of this invention include the hydroxides of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methylglucamine; L-glutamine; N-methylpiperazine; morpholine; ethylenediamine; N-benzylphenethylamine; tri(hydroxymethyl)aminomethane; and the like. (See for example, "Pharmaceutical Salts," J. Pharm. Sci. (1977) 66(1): 1–19.)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

A preferred embodiment of the present invention is a compound of formula I wherein $R_6$ is OH or SH; $R_2$ and $R_8$ are $NH_2$, n is one, and Ar is 2- or 3-thienyl. A more preferred embodiment is 2-amino-7-(2-thienylmethyl)-4-pyrrolo[2,3-d)]pyrimidone.

The compositions having compounds of the formula I of the present invention are shown to exhibit significant enzyme inhibition activity and cytotoxicity activity. In the purine nucleoside phosphorylase (PNP-4) enzyme assay, an $IC_{50}$ is achieved at a dose of 1.0 micromoles on a selected compound of the present invention. PNP-4 activity for the compound of formula I is measured radiochemically by measuring the formation of [$^{14}$—C]hypoxanthine from [$^{14}$—C]inosine [Biomedicine, 33, 39 (1980)] using human erythrocyte as the enzyme source.

It is known that an in vivo inhibition of purine nucleoside phosphorylase (HPLC-1) enzyme assay may also be used essentially as disclosed in the Annals of New York Academy of Sciences, Volume 451, Page 313 (1985) to further show the activity for compositions of the compounds of formula I of the present invention. The present invention compositions also are generally shown by a standard test (HTBA-1) [Science, 214, 1137, (1981)] to be selectively cytotoxic for T-cells in the presence of 2'-deoxyguanosine at a similar concentration range and nontoxic to B-cell in the presence of the same amount of 2'-deoxyguanosine by the compound of Example 2, thus demonstrating utility for the compounds of formula I in pharmaceutical compositions as described herein. Since PNP inhibition and removal of T-cells or modulation of T-cells are known to be characteristics of compounds beneficial in the treatment of psoriasis, rejection phenomenon in transplantation, and autoimmune diseases, the present invention compositions of compounds being selectively cytotoxic to T-cells and being PNP inhibitors will, therefore, also be useful in such treatment. For example, 8-Aminoguanosine, a known PNP-inhibitor, has been shown to be efficacious for inhibiting rejection of skin graft in dogs [J. B. Benear, et al, Transplantation, 1986, 41: 274]. Clinically it has been shown that modulation and/or removal of T-cells by thoracic duct drainage, lymphapheresis or total lymphoid irradiation gave partial to complete relief from rheumatoid arthritis in patients who were totally refractory to other forms of therapy (A. Tanay, et al, *Arthritis and Rheumatism*, Vol. 30, No. 1, p. 1 (1987). S. Strober, et al, *Annual of Internal Medicine*, V-102, No. 4, 441–449 (1985); H. G. Nusslein, et al, *Arthritis and Rheumatism*, V-28, No. 11, 1205–1210 (1985); E. Brahn, et al, ibid, V-27, No. 5, 481–487 (1984), and J. Karsh, et al, ibid, V-24, No. 7, 867–873 (1981)). Cyclosporin A, a T-cell modulator, showed beneficial effects in the treatment of juvenile diabetes. (A. Assan, et al, The Lancet, January 12, p. 67 (1985).) Additionally, cyclosporin A is presently the drug of choice for the prevention of transplant rejection, (R. M. Merion, et al, *New Eng. J. Med.*, (1984) 148). More recently, cyclosporin A is shown to be useful to treat psoriasis. Further, it is suggested the cyclosporin therapy is shown to markedly reduce activated T-cells in psoriatic lesions. Therefore, it is reasonable to believe the basis of the successful treatment of psoriasis in modulation of T-cell activity as shown by compounds in the present invention composition. (See C. N. Ellis, et al, JAMA, V-256, No. 22, Dec. 12, 1986, pp. 3110-3116.) Finally, cyclosporin A is shown to be efficacious in rheumatoid arthritis. (M. E. Weinblatt, et al, *Arthritis and Rheumatism,* V-30, No. 1, pp. 11-17 (January, 1987); O. Forre, et al, *Arthritis and Rheumatism,* V-30, No. 1, pp. 88-92 (January, 1987); M. Dougados, et al, *Arthritis and Rheumatism,* Vol. 30, No. 1, pp. 83-87 (January, 1987).

Representative examples from the present invention are shown in the following activity table to provide the activity discussed above.

ACTIVITY TABLE $$\begin{array}{c}\text{HN}\underset{H_2N}{\overset{\displaystyle\|}{\diagup}}\underset{N}{\overset{\text{O}}{\diagdown}}\diagdown\diagup\underset{Ar}{\diagdown}\diagup\overset{H}{\underset{N}{\diagdown}}{-}R_8\end{array}$$

| Number | R$_7$ | R$_8$ | Ar | PNP-4 IC$_{50}$ (μM) | HTBA-1 T-Cell + 10 μM 2'-d Gua; IC$_{50}$ μM |
|---|---|---|---|---|---|
| 2 | H | H | 2-Th | 1.0 | 2.3 |

Th = Thiophene

In vivo studies based on the above noted disclosures may be used to determine activity in the particular disease states noted.

Since T-cells play a central role in immune response, use of the compounds of the invention is contemplated for the immunoregulation to prevent rejection in transplantation or in the treatment of psoriasis and in the treatment of autoimmune disease such as rheumatoid arthritis, systemic lupus erythrematosus, inflammatory bowel disease, multiple sclerosis, myasthemia gravis, gout or gouty arthritis, juvenile diabetes, cancer, and viral diseases. The present invention thus includes compositions containing a compound of formula I in treating rejection of transplantation or disease such as psoriasis in humans or autoimmune disease characterized by abnormal immune response in primates or humans. According to this aspect of the invention, the properties of the compounds of the invention are utilized by administering to a warmblooded animal an effective amount of a pharmaceutical composition containing as the active ingredient at least about 0.1 percent by weight, based on the total weight of the composition of at least one such compound of the invention.

Pharmaceutical compositions of the invention can be formulated in any suitable way, preferably with an inert carrier for administration orally, parenterally, ophthalmically, topically, or by suppository.

For example, the compounds of the present invention are formulated into dosage forms such as tablets or syrups by blending with an inert pharmaceutical carrier such as lactose or simple syrup by methods well-known in the art. For injectable dosage forms, they are formulated with vehicles such as water, propylene glycol, peanut oil, sesame oil, and the like. In these dosage forms the active ingredient is from about 0.05 grams to 0.5 grams per dosage unit.

The present invention is further illustrated by way of the following examples.

EXAMPLE 1

2-Amino-6-[(2-thienylmethyl)amino]-4-pyrimidinol

2-Amino-6-chloro-4-pyrimidinol, monohydrate (85%, 100 g, 0.5197 mol) was suspended in methoxyethanol (700 ml) and 2-thienylmethylamine (96%, 61.3 g, 0.5197 mol) was added to the suspension. The mixture was heated under reflux for two hours and then 73 ml (d=0.726; 0.52 mol) of triethylamine was added and the refluxing continued for an additional 18 hours. The reaction mixture was poured into ice water (1000 ml), acidified with acetic acid (ph 4.0) and the precipitated solid was filtered, washed, and dried. Yield: 110 g (72.6%). This was used in the next step without further purification.

EXAMPLE 2

2-Amino-7-(2-thienylmethyl)-4-pyrrolo[2,3-d]pyrimidones

Chloroacetaldehyde dimethyl acetal (14 ml) was added to water (50 ml) and concentrated HCl (2.0 ml). The mixture was heated at reflux temperature for 30 minutes and then neutralized with sodium acetate (10 g). The resulting solution was added in one portion to a mixture of 2-amino-4-(2-thienylmethyl)-6-pyrimidone (10 g; 45 mmol), sodium acetate (5.0 g) and hot water (50 ml). The mixture was allowed to stir on a steam bath (80° C.) for 30 minutes, and the precipitated solid was filtered, washed with water, and dried in vacuo. The crude product was dissolved in methanol and concentrated HCl and treated with charcoal to remove coloring matter. The product (3.2 g) thus obtained was recrystallized from methanol and 1N HCl (100 ml) to give 1.68 g (13.5%) of the desired product as light brown solid, mp 243°-245° C. (dec).

2-Amino-4-chloro-6-[2-thienylmethyl)amino]-5-(2,2-diethoxyethyl)pyrimidine

A solution of 2-amino-4,6-dichloro-5-(2,2-diethoxyethyl)pyrimidine (M. Legraverend, et al, *J. Med. Chem.,* 1985, 28: 1477) (906 mg, 3.20 mmol) in 40 ml of n-butanol containing Et$_3$N (1 ml) and 2-thienylamine (425 mg, 3.75 mmol) was heated at 100° C. for 48 hours. The reaction mixture was cooled to 25° C. and concentrated. The residue was cooled to 25° C. and concentrated. The residue was purified by column chromatography over silica gel and eluted with chloroform to give the desired product (1.045 g) (91.5%) as a yellow oil.

2-Amino-4-chloro-7-(2-thienylmethyl)pyrrolo[2,3-d]pyrimidine

A suspension of 2-amino-4-chloro-6-[(2-thienylmethyl)amino]-5-(2,2-diethoxyethyl)pyrimidine (1.0 g, 2.80 mmol) in 65 ml of 0.3N HCl and ethanol (2.25:1) was stirred at 25° C. for 24 hours. The reaction mixture was neutralized with ammonium hydroxide solution and the product collected by filtration. TLC analysis showed that the reaction was not complete, so, the product was resuspended in 50 ml of 0.2N HCl and stirred for 48 hours. The reaction mixture was neutralized with NH$_4$OH solution and concentrated. The residue was taken up in water and then evaporated to dryness to give yellow solid (573 mg) (77.3%). This was used in the next step without further purification.

2-Amino-7-(2-thienylmethyl)-4-pyrrolo[2,3-d]pyrimidone

2-Amino-4-chloro-7-(2-thienylmethyl)pyrrolo[2,3-d]pyrimidine (563 mg, 2.10 mmol) was suspended in 30 ml of 1N HCl and ethanol (1:1) and the mixture was heated at reflux for 8 hours. Removal of solvent gave a residue which was chromatographed over silica gel and eluted with a mixture of hexane-ethyl-acetate (10:1) to give 139 mg of a mixture of 4-chloro and 4-ethoxy derivatives. So, it was dissolved in 30 ml of 3N HCl and the solution was heated to reflux for 2 hours and then allowed to cool. The precipitated solid was filtered and then recrystallized from methanol-1N HCl (1:1) mixture to give 55 mg of the desired product was hydrochloride salt, mp 235°-237° C. (dec).

We claim:

1. A compound of the formula (I)

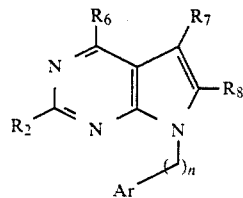

wherein $R_6$ is OH or SH, $R_2$ is hydrogen or $NH_2$, $R_7$ and $R_8$ are independently hydrogen or $NH_2$ with the proviso that both cannot be $NH_2$ at once, n is an integer of from one through four, Ar is (i) 2- or 3-thienyl, or (ii) 2- or 3-furanyl; or a pharmaceutically acceptable base or acid addition salt thereof.

2. A compound of claim 1 wherein $R_7$ is hydrogen.
3. A compound of claim 2 wherein $R_8$ is hydrogen.
4. A compound of claim 2 wherein $R_8$ is amino.
5. A compound of claim 3 and being 2-amino-7-(2-thienyl-methyl)-4-pyrrolo[2,3-d]pyrimidone.
6. A compound of claim 5 and being the hydrochloride salt thereof.
7. A pharmaceutical composition for treating psoriasis, autoimmune diseases or rejection of transplantation comprising an antipsoriatic, antiautoimmune disease or antirejection of transplantation effective amount of a compound of formula (I)

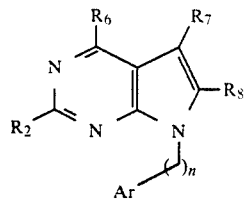

or a pharmaceutically acceptable base or acid addition salt thereof; wherein $R_6$ is OH or SH, $R_2$ is hydrogen or $NH_2$, $R_7$ and $R_8$ are independently hydrogen and $NH_2$ with the proviso that both cannot be $NH_2$ at once, n is an integer of from one to four, Ar is (i) 2- or 3-thienyl, or (ii) 2- or 3-furanyl and a pharmaceutically acceptable carrier.

8. A method for treating autoimmune disease or rejection of transplantation which comprises administering a composition of claim 7 in unit dosage form.

* * * * *

UNITED STATES PATENT AND TRADEMARK OFFICE
CERTIFICATE OF CORRECTION

PATENT NO. : 4,921,858
DATED : May 1, 1990
INVENTOR(S) : T. C. Malone, et al

It is certified that error appears in the above—identified patent and that said Letters Patent is hereby corrected as shown below:

In column 1, line 63, change "Ser. No. PD-3557" to "U.S. Application Serial No. 07/336,585 filed April 10, 1989, now U.S. Patent No. 4,923,872 issued May 8, 1990".

Signed and Sealed this

Twelfth Day of May, 1992

Attest:

DOUGLAS B. COMER

*Attesting Officer*     *Acting Commissioner of Patents and Trademarks*